United States Patent
Williams

(10) Patent No.: US 10,743,919 B1
(45) Date of Patent: Aug. 18, 2020

(54) NAVIGATED PERCUTANEOUS LUMBAR AND THORACIC SPINE FACET FUSION

(71) Applicant: Seth K. Williams, Madison, WI (US)

(72) Inventor: Seth K. Williams, Madison, WI (US)

(73) Assignee: Seth K. Williams, Madison, WI (US)

( * ) Notice: Subject to any disclaimer, the term of this patent is extended or adjusted under 35 U.S.C. 154(b) by 0 days.

(21) Appl. No.: 16/680,719

(22) Filed: Nov. 12, 2019

(51) Int. Cl.
| | | |
|---|---|---|
| *A61B 17/70* | (2006.01) | |
| *A61B 17/88* | (2006.01) | |
| *A61B 34/20* | (2016.01) | |
| *A61B 34/00* | (2016.01) | |
| *A61B 90/00* | (2016.01) | |
| *A61B 17/00* | (2006.01) | |
| *A61B 17/56* | (2006.01) | |
| *A61B 17/17* | (2006.01) | |
| *A61B 34/32* | (2016.01) | |

(52) U.S. Cl.
CPC .......... *A61B 17/7064* (2013.01); *A61B 34/20* (2016.02); *A61B 34/25* (2016.02); *A61B 17/00234* (2013.01); *A61B 17/1757* (2013.01); *A61B 34/32* (2016.02); *A61B 34/76* (2016.02); *A61B 2017/00933* (2013.01); *A61B 2017/564* (2013.01); *A61B 2090/374* (2016.02); *A61B 2090/376* (2016.02); *A61B 2090/378* (2016.02); *A61B 2090/3762* (2016.02); *A61B 2090/392* (2016.02); *A61B 2090/3983* (2016.02)

(58) Field of Classification Search
CPC .......... A61B 17/7064; A61B 17/00234; A61B 17/1757; A61B 34/20; A61B 34/25; A61B 34/32; A61B 34/76; A61B 2090/374; A61B 2090/376; A61B 2090/3762; A61B 2090/378; A61B 2090/392; A61B 2090/3983; A61B 2017/00933; A61B 2017/564
USPC ....... 600/204, 208, 411, 414, 416, 417, 424, 600/426, 429
See application file for complete search history.

(56) References Cited

U.S. PATENT DOCUMENTS

| | | |
|---|---|---|
| 2008/0132904 A1 | 6/2008 | Usher et al. |
| 2008/0255667 A1 | 10/2008 | Horton |
| 2009/0036926 A1 | 2/2009 | Hestad |
| 2009/0036927 A1 | 2/2009 | Vestgaarden |
| 2009/0076551 A1 | 3/2009 | Petersen |
| 2010/0268228 A1 | 10/2010 | Petersen |
| 2011/0288588 A1 | 11/2011 | Chin et al. |
| 2012/0253353 A1 | 10/2012 | McBride |
| 2014/0135927 A1 | 5/2014 | Pavlov et al. |

(Continued)

OTHER PUBLICATIONS

Non-Final Office Action issued on U.S. Appl. No. 15/407,625, dated Jan. 31, 2019.

*Primary Examiner* — Pedro Philogene
*Assistant Examiner* — David C Comstock
(74) *Attorney, Agent, or Firm* — Bell & Manning, LLC

(57) ABSTRACT

A system for percutaneous or open facet joint fusion includes an imaging system configured to identify a docking location on a facet joint between a first vertebra and a second vertebra of a patient. The system also includes a cannula configured to be positioned at the docking location on the facet joint. The system further includes a rotary tool that is configured to mount within the cannula. The rotary tool is configured to create a void in the facet joint by way of the cannula, where the void is configured to receive a bone graft or bone growth promoting material.

18 Claims, 9 Drawing Sheets

(56) References Cited

U.S. PATENT DOCUMENTS

| | | |
|---|---|---|
| 2016/0175113 A1 | 6/2016 | Lins |
| 2016/0270772 A1* | 9/2016 | Beale ............... A61B 17/56 |
| 2016/0324561 A1 | 11/2016 | Vouaillat |
| 2017/0135704 A1 | 5/2017 | Abbasi |
| 2017/0209158 A1 | 7/2017 | Williams |
| 2018/0168539 A1* | 6/2018 | Singh ............... A61B 8/4483 |
| 2018/0279993 A1* | 10/2018 | Crawford .......... A61B 17/7082 |

* cited by examiner

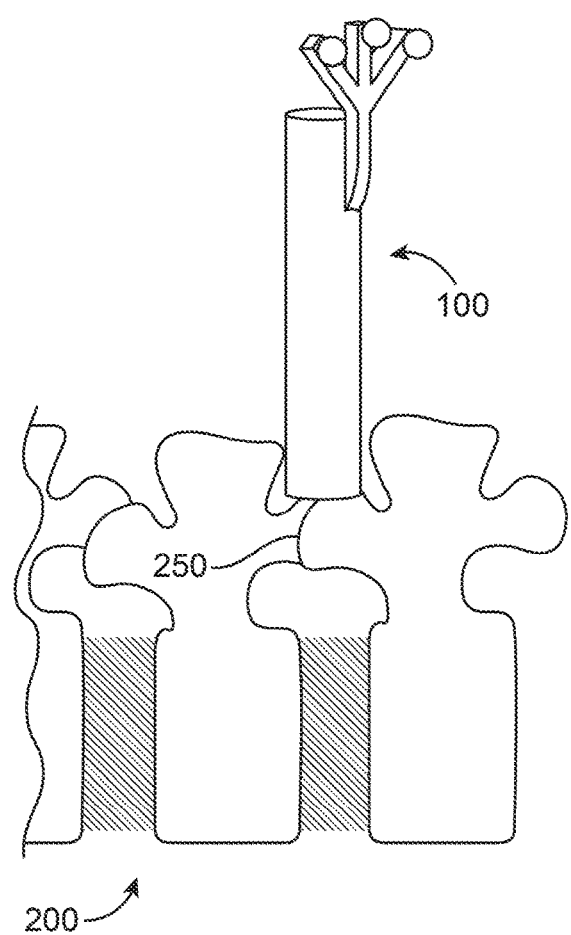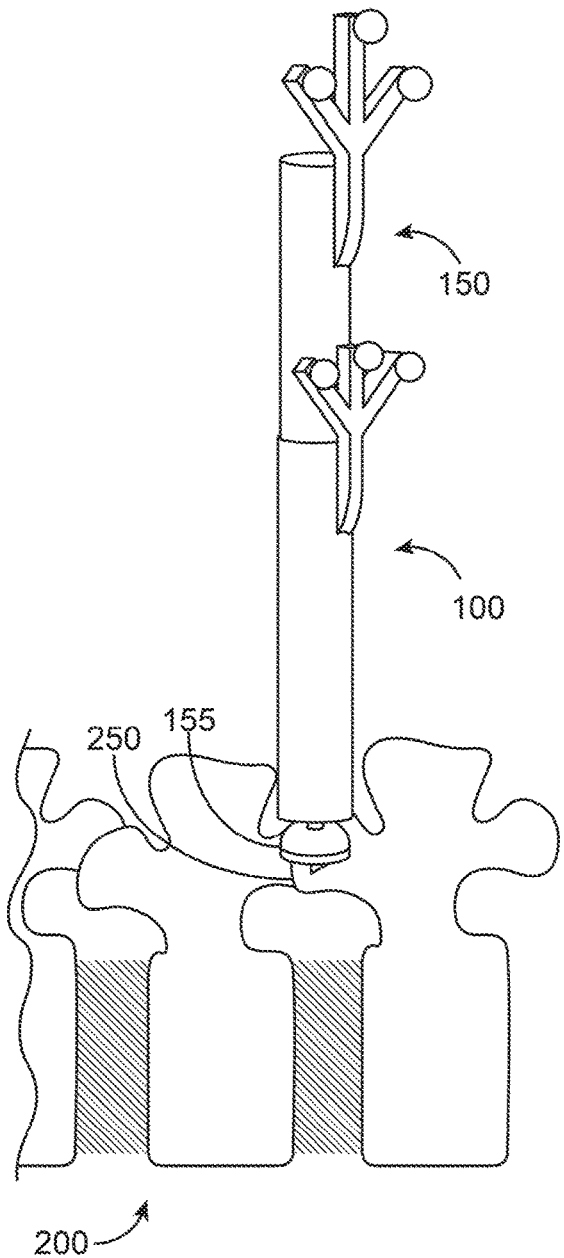
FIG. 3A
FIG. 3B

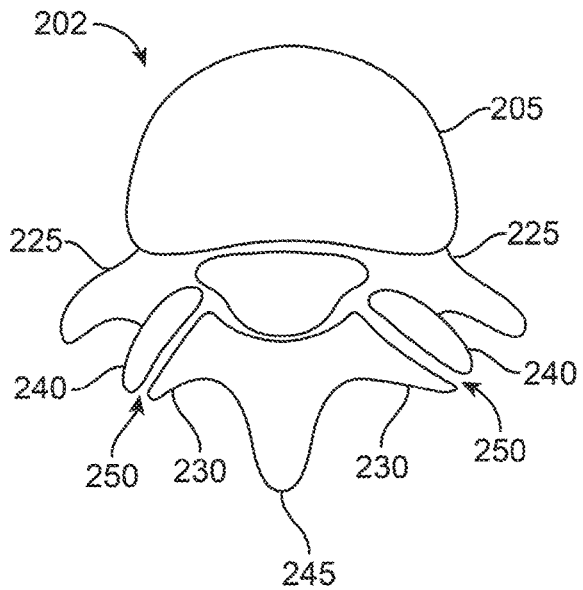
FIG. 4C
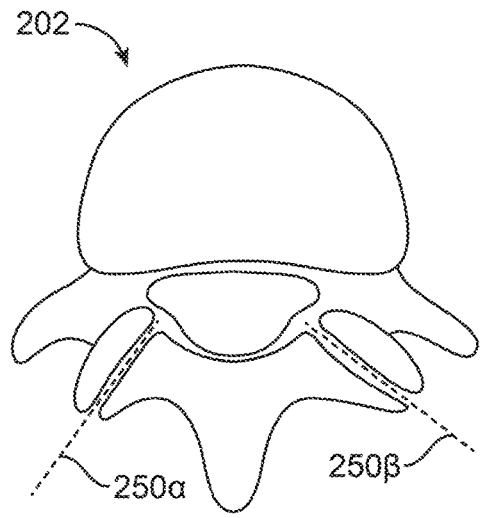
FIG. 4D
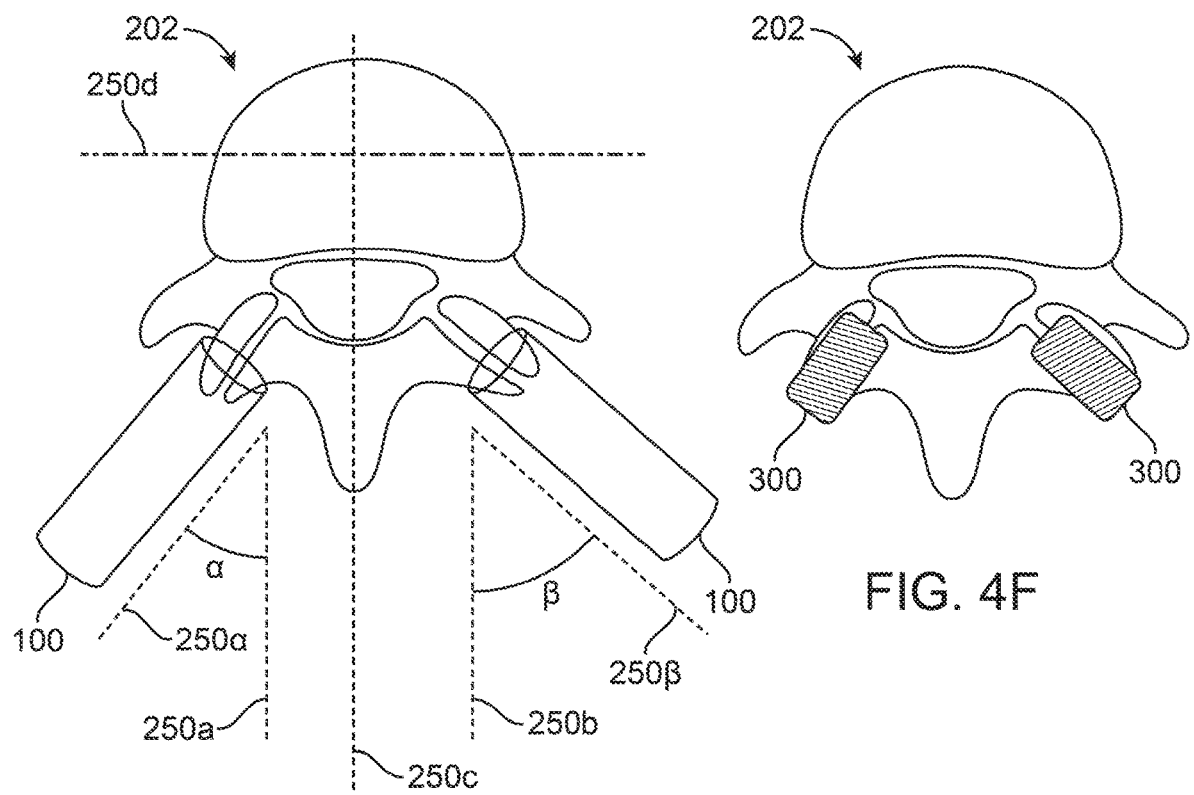
FIG. 4E
FIG. 4F

NAVIGATED PERCUTANEOUS LUMBAR AND THORACIC SPINE FACET FUSION

BACKGROUND

The lumbar spine refers to the lower back, and is where a human spinal column curves inward toward the abdomen. The lumbar spine, which typically starts five to six inches below the shoulder blades, connects with the thoracic spine at the top and the sacral spine at the bottom. A human lumbar spine typically includes 5 vertebrae, although some individuals have 6 vertebrae in their lumbar spine. A typical single-level spinal segment includes a disk that is located between a cephalad vertebra and a caudal vertebra. The cephalad and caudal vertebrae are connected to each other primarily through the disk anteriorly and through a left and right facet joint posteriorly. The vertebrae are stabilized by ligaments, muscles, and their intrinsic facet geometry. The facet joints are bony projections from the posterior vertebrae that are capped with cartilage, and that articulate with each other. The disk and facet joints allow some mobility between the vertebral segments, while in tandem with the ligaments and muscles, also provide spinal stability. There are several different conditions that can cause pain in the lumbar and thoracic spine, including disk problems such as degenerative disk disease, facet degeneration, scoliosis and other deformities, trauma, tumor, infection, spondylolisthesis, stenosis, etc.

Non-operative treatments such as physical therapy, medications, and exercise may be appropriate for some of these conditions, but sometimes it is determined that surgery is necessary. A lumbar and/or thoracic spine fusion can be used to help alleviate pain and/or stabilize the spine in some individuals who are suffering from the aforementioned ailments. A spinal fusion may be performed in a variety of manners, including a conventional extensile open surgical approach through a midline posterior incision. Alternatively, a minimally invasive approach may be utilized, using a series of smaller incisions in order to minimize the physiological burden of surgery.

Spinal instrumentation systems, for example, pedicle screws and rods, are often used to stabilize the spine and improve the fusion rate, in both open and minimally invasive percutaneous procedures. Spinal instrumentation can be placed through a single extensile incision in conventional open surgery, or may be placed through a series of small incisions, which is commonly referred to as percutaneous pedicle screw instrumentation. The spinal instrumentation provides the stability component of the fusion operation, but a successful fusion also depends on a biological component, which is new bone growth between vertebral segments. In order for this new bone growth to occur and achieve fusion, the biological environment must favor bone growth. This biological component of the fusion typically depends on placement of bone graft or a bone growth promoting material between vertebral segments, which stimulates new bone growth from one vertebra to the next and results in a spinal fusion.

SUMMARY

An illustrative system for percutaneous or open facet joint fusion includes an imaging system configured to identify a docking location on a facet joint between a first vertebra and a second vertebra of a patient. The system also includes a cannula configured to be positioned at the docking location on the facet joint. The system further includes a rotary tool that is configured to mount within the cannula. The rotary tool is configured to create a void in the facet joint by way of the cannula, where the void is configured to receive a bone graft or bone growth promoting material.

An illustrative method for performing percutaneous or open facet joint fusion includes identifying, by an imaging system, a docking location on a facet joint between a first vertebra and a second vertebra of a patient. The method also includes docking a cannula at the docking location on the facet joint. The method further includes creating, by a rotary tool that is configured to mount within the cannula, a void in the facet joint, where the void is configured to receive a bone graft or bone growth promoting material.

The foregoing is a summary of the disclosure and thus by necessity contains simplifications, generalizations, and omissions of detail. Consequently, those skilled in the art will appreciate that the summary is illustrative only and is not intended to be in any way limiting. Other aspects, features, and advantages of the devices and/or processes described herein, as defined by the claims, will become apparent in the detailed description set forth herein and taken in conjunction with the accompanying drawings.

BRIEF DESCRIPTION OF THE DRAWINGS

The present disclosure will become more readily apparent from the specific description and the following drawings, in which:

FIG. 3A depicts a lateral view of the lumbar spine segment, including a facet joint, and a cannula docked onto the facet joint, in accordance with an illustrative embodiment.

FIG. 3B depicts a lateral view of the lumbar spine segment with a facet joint, a cannula docked onto the facet joint, and the rotary tool inserted into the cannula, in accordance with an illustrative embodiment.

FIG. 4C is a first cross-sectional depiction of a vertebra, with facet joints (as shown in FIG. 4A) in accordance with an illustrative embodiment.

FIG. 4D is a second cross-sectional depiction of a vertebra, with facet joints (as shown in FIG. 4A) in accordance with an illustrative embodiment.

FIG. 4E is a cross-sectional depiction of a vertebra with cannulas docked on the facet joints in accordance with an illustrative embodiment.

FIG. 4F is a cross-sectional depiction of a vertebra with bone graft or bone growth promoting material placed in voids in the facet joints in accordance with an illustrative embodiment.

DETAILED DESCRIPTION

Figure 1A:
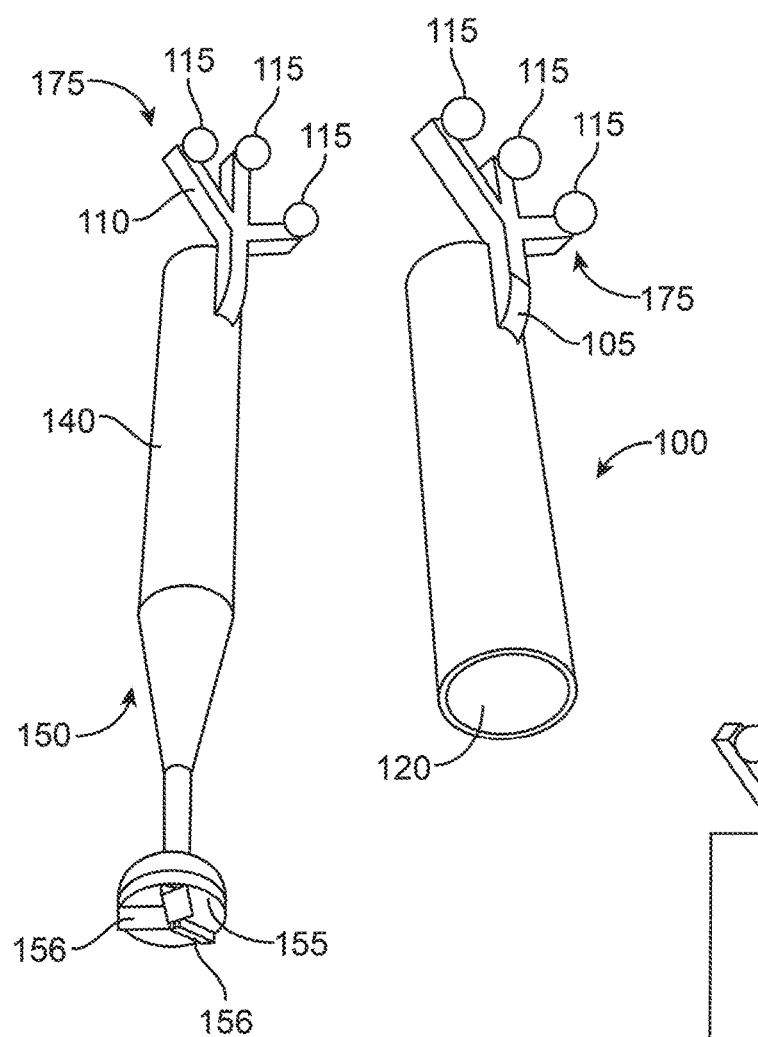
FIG. 1A depicts a first view of a fusion system that includes a cannula and a rotary tool in accordance with an illustrative embodiment.

Existing minimally invasive lumbar and thoracic fusion techniques rely on an interbody fusion, whereby the disk between the two vertebrae being fused is removed and replaced with structural and/or biological material (i.e., bone graft or a bone growth promoting material) to promote bone growth across the intervertebral space. Described herein are methods and systems for performing a percutaneous or open facet fusion that depends on intra-operative stereotactic navigation and/or other imaging technique(s) to accurately target the facet joint.

Traditional posterior lumbar and thoracic spinal fusions are typically performed through one or more incisions placed on the posterior aspect of the spine. A single incision can be made in the midline and then the soft tissues stripped off the posterior aspect of the spine to expose the transverse processes of two or more spinal levels. The transverse processes are decorticated and bone graft or bone growth promoting material is placed between the transverse processes, performing what is referred to as a posterolateral fusion. An open posterior spinal fusion may also be performed by accessing the disk space, which involves navigating past the neural elements, removing the disk material, and placing bone graft or bone growth promoting material within the intervertebral space. Alternatively, for a minimally invasive fusion, multiple incisions can be made through the skin or fascia off the midline, the muscles split along natural planes rather than stripped, and the interbody space exposed and the interbody fusion performed in a similar manner to the open interbody fusion procedure. The minimally invasive technique also involves navigation past the neural elements. With minimally invasive techniques, a reliable method has not been developed to perform a fusion that does not utilize the interbody space.

In some procedures, percutaneous pedicle screws are placed posteriorly through small incisions, each incision accommodating one, two, or rarely three, pedicle screws. These screws are then connected to each other with rods, thus stabilizing the spine. One of the more common reasons to place the pedicle screws and rods is to stabilize the spine as part of a spinal fusion procedure. Interbody fusion across the disk space can be performed through an anterior, anterolateral, lateral, or posterior technique, and under these circumstances, posterior percutaneous pedicle screws can then be placed through separate small incisions, thus stabilizing the spine.

A drawback to traditional intervertebral fusion is that the disk space is located relatively deep within the human body, and access to the disk space is therefore sometimes risky or difficult. With a posterior surgical approach, the surgeon must navigate past the neural elements in order to access the disk space, and/or the muscles stripped off the posterior aspect of the spine in order to access the transverse processes. With an anterior, anterolateral, or lateral surgical approach, the surgeon must dissect through the abdominal cavity or retroperitoneal space or the chest cavity, placing many anatomic structures at risk. Described herein is an alternative fusion system and technique that employs a posterior approach to the spine, but avoids navigating past the neural elements, and avoids extensive muscle stripping when performed percutaneously. This percutaneous spinal fusion technique does not require access to the disk space, instead relying on fusion of the facet joints, and involves less-invasive muscle splitting rather than muscle stripping when performed percutaneously. This described technique allows for a posterior facet fusion through the same incision(s) used to place percutaneous pedicle screws, without accessing the interbody space, thus minimizing surgical trauma to the patient.

Described herein are a system and technique to perform a facet fusion through small incisions, allowing for a minimally invasive facet fusion, or via more conventional open techniques. The main benefits of this technique are the simplicity and low risk, because it does not involve accessing the disk space, and therefore avoids the associated issues that can arise when navigating past the neural elements. When performed percutaneously, either on their own or as an adjunct to an anterior or lateral interbody fusion, the same small incisions that are routinely placed during placement of percutaneous pedicle screw instrumentation are utilized for the facet fusion. The technique is primarily designed to be used with the described minimally invasive percutaneous approach, but can also be employed in more conventional open surgical techniques. It should be understood that the terminology used in this present disclosure is for the purpose of description by way of example and is not intended to be limiting in any way.

In one embodiment, to perform the percutaneous facet fusion, an incision is made through the skin, subcutaneous tissues, and fascia in the standard size and fashion used to place a pedicle screw directly below the facet to be fused. The percutaneous pedicle screw incision is placed in a manner well known to those schooled in the art. The percutaneous pedicle screw incision is usually approximately 1 centimeter (cm) in length, but can be shorter or longer. When a percutaneous facet fusion is performed, the fusion is generally performed prior to pedicle screw placement, but could be performed after pedicle screw placement if the incision was extended. After making the incision, blunt dissection can be performed down to the facet joint, and a cannula of approximately 5-10 millimeters (mm) in diameter is placed through the incision and docked onto the facet joint to be fused, using stereotactic navigation or other imaging techniques to position the cannula accurately. For example, an imaging system can be used to identify the cannula and/or anatomical features within the patient, such as a docking location on the facet joint. The cannula can thus be docked at a desired location and at a desired angle via the imaging system. In other embodiments, cannula placement can also be done freehand using only tactile feedback and/or via adjunctive fluoroscopy or other imaging guidance.

In some embodiments, the cannula is placed using stereotactic intraoperative 3-dimensional navigation to accurately dock the cannula on the facet joint to be fused. Accurately docking the cannula entails positioning the cannula onto the facet joint at an angle that matches or closely matches the angle of the facet joint, which can vary from person to person and from one vertebral level to the next and from side to side at a single vertebral level. Matching, or closely matching, the facet joint orientation ensures that when the rotary tool is passed through the cannula and creates a void in the facet joint, bone and cartilage are removed in similar proportions from those portions of the cephalad and caudal vertebral features that comprise the facet joint.

In one embodiment, an end of the cannula that contacts the bone can include one or more sharp points or spikes or teeth that contacts the facet joint, in order to prevent migration of the cannula. Alternatively, such points/spikes may not be included on the cannula. In an alternative embodiment, the cannula may be held in place with an articulating mechanical arm that is anchored to the surgical bed on one end and attached to the cannula at the opposite end. In alternative embodiments, the cannula may be positioned and held in place with an articulating mechanical arm that is anchored to a surgical robot on one end and attached to the cannula at the opposite end.

In some embodiments, a blunt inner stylette may be placed in the cannula to facilitate blunt dissection down to the facet joint, or the cannula can be placed without the inner stylette. Once the cannula is appropriately positioned on the facet joint, using tactile feedback and a navigation system, and the inner stylette removed if used, a rotary tool (e.g., burr, drill, etc.) is advanced through the cannula approximately 5-8 mm into the facet joint. The rotary tool bit depth can be determined based on pre-operative imaging and/or optionally on intraoperative navigation. The rotary tool is then removed and bone graft or other bone growth promoting material placed through the cannula with a tamp or other implement and into the cylindrical void left by the rotary tool bit.

The bone graft or bone growth promoting material can be non-structural as in the case of an allograft bone putty or bone graft fragments, or can be more structural in nature as in the case of a pre-fabricated allograft that would be press-fit into the void. Once the bone graft or other bone growth promoting material is placed in the void, the cannula is removed, and the percutaneous pedicle screw is then placed in the standard fashion through the same incision, in a manner well known to those schooled in the art. Because the facet joint is adjacent to the pedicle screw starting point, the elasticity of the skin and the soft tissues allows for translation of the incision cephalad and caudal a sufficient distance to allow both the facet fusion and percutaneous pedicle screw placement to be performed through the same incision.

In some embodiments, the facet fusion can be performed during more conventional open surgery, rather than percutaneously. In this embodiment, the facet is exposed in the standard fashion through an open posterior extensile approach, and the cannula docked onto the facet under direct visualization, with navigation to accurately determine the proper angle to drill/burr into the facet joint. The facet joint orientation and angle can vary from person to person, from one vertebral level to the next within the same person, and from side to side at a single vertebral level within the same person. Matching, or closely matching, the facet joint angle ensures that when the rotary tool is passed through the cannula and creates a void in the facet joint, bone and cartilage is removed in similar proportions from those portions of the cephalad and caudal vertebral features that comprise the facet joint.

Standard human facet joints are covered with a soft tissue capsule, so that the facet joint angle cannot be visualized during surgery unless the capsule is removed during open surgery. When a facet fusion is performed percutaneously, the incisions are small and it is not typically possible for the surgeon to clearly visualize the facet angle, even with the facet capsule removed. The use of intraoperative navigation systems, in particular those based on computed tomography and/or magnetic resonance imaging, allows the surgeon to visualize the facet joint angle during surgery without actually exposing the facet joint. The surgeon is then able to insert and position the cannula in a manner that matches the facet joint angle, allowing for precise void creation in the facet joint in order to place bone graft or bone growth promoting material so that the bone graft or substitute comes into contact with freshly drilled or burred bone from both the cephalad and caudal vertebral components that make up the facet joint.

In one embodiment, the surgeon can use a virtual projection from a navigated instrument overlayed on a computed tomography or magnetic resonance image in order to match the facet joint angle and orientation. The surgeon can then follow this pathway when making the incision and docking the cannula. If the cannula is docked at an angle different from the facet joint angle, then the void created in the facet joint by the rotary tool may not sufficiently include the desired amount of one or the other vertebral features that make up the facet joint, making fusion between the two vertebral segments less likely. Once the cannula is docked at the appropriate angle, the facet fusion then proceeds in the above described fashion, by burring or drilling into the facet joint, placing the bone graft or bone growth promoting material into the cylindrical void left by the burr or drill bit, and optionally placing a pedicle screw as part of a spinal instrumentation construct.

The facet fusion may be performed unilaterally or bilaterally, and may be performed with or without spinal instrumentation, though it is designed primarily to be performed bilaterally at the spinal level that will be subsequently stabilized with spinal instrumentation.

Figure 1B:
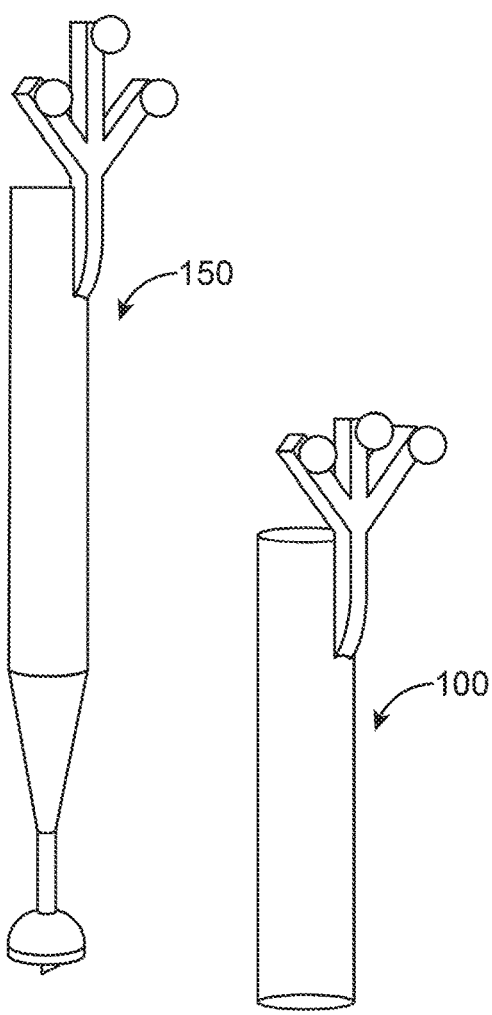
FIG. 1B depicts a second view of the fusion system that includes the cannula and the rotary tool in accordance with an illustrative embodiment.

FIG. 1A depicts a first view of a fusion system that includes a cannula 100 and a rotary tool 150 in accordance with an illustrative embodiment. FIG. 1B depicts a second view of the fusion system that includes the cannula 100 and the rotary tool 150 in accordance with an illustrative embodiment. In some embodiments, the cannula is a cylinder with a central hole 120, through which a burr or drill bit (or other rotary tool) and/or bone graft or a bone growth promoting material can be passed. In some embodiments, the rotary tool 150 includes a tool handle 140 and a rotary tool bit 155 with cutting features 156. In some embodiments, the cannula 100 may include a navigation arm 175 that includes one or more passive markers 115 attached to the cannula 100 via a plurality of arms 105. In some embodiments, the rotary tool 150 also (or alternatively) includes a navigation arm 175 that includes passive markers 115 attached to the rotary tool 150 via a plurality of arms 110. The arms 105 and 110, and attached markers 115, may be tracked in space by an imaging system (camera, laser, etc.) that communicates the position and orientation of the cannula and the rotary tool during surgery, allowing for stereotactic navigation of the surgical instruments when paired with intraoperative imaging and a reference frame attached to the patient's body. The reference frame is used to pair the patient's anatomy to the imaging system. This allows the computer software to overlay a virtual depiction of a navigated surgical instrument onto whatever images are being used for navigation, be it fluoroscopy, computed tomography images, or magnetic resonance images. The surgeon then uses the virtual overlay of the surgical instruments to perform the surgery. The reference frame is attached to the patient's body by one of several available mechanisms, such as an array of markers attached to the skin with adhesive, or an array of markers attached to bone by a post or a screw (or screws) or a clamp. In alternative embodiments, a reference frame may not be used.

In an illustrative embodiment, the passive markers positioned on the rotary tool 150 and/or the cannula 100 can be in the shape of spheres. Alternatively, a different shape may be used, such as cubical, cylindrical, rectangular parallelepiped, pyramidal, etc. Each of the passive markers on the rotary tool and/or the cannula can be the same shape or can have different shapes, depending on the implementation. Additionally, although 3 passive markers are depicted on the cannula and on the rotary tool, different numbers may be used in alternative embodiments, such as 1, 2, 4, 5, 10, etc. The cannula can have a different number, size, position, and/or shape of passive markers than the rotary tool in some embodiments, or alternatively, both instruments can have the same marker configuration.

In another illustrative embodiment, the passive marker(s) and/or the navigation arms on which they are mounted are movable such that a surgeon is able to manipulate their position before or during a procedure. In one embodiment, a wire can be connected to a manual control (e.g., handle, crank, lever, knob, switch, etc.) and to the passive markers and/or navigation arms. The surgeon can manipulate the control (which can be positioned on the cannula, on the rotary tool, or on both) to position the passive markers/navigation arms so that they do not injure the patient or prevent the end of the rotary tool from making contact with a desired portion of a vertebra. In an alternative embodiment, an actuator and power source (e.g., battery) can be incorporated into the navigation arm(s) and/or the passive markers to facilitate remote and/or automated movement control of the markers. For example, in one embodiment, a computer in communication with the imaging system can automatically detect both anatomical structures of the patient and the passive markers, and can position the passive markers to avoid the anatomical structures during entry, use, and removal of the rotary tool/cannula.

Figure 1C:
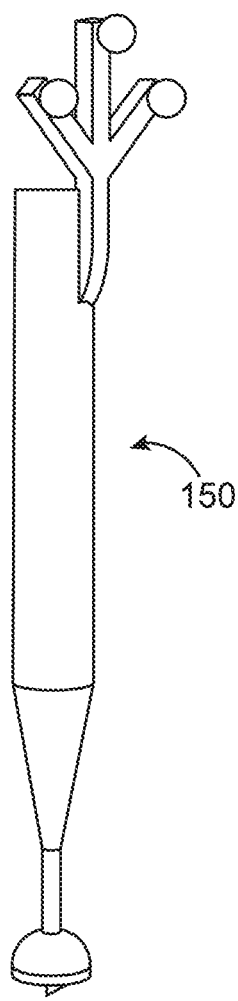
FIG. 1C depicts the rotary tool in anticipation of being inserted into the central hole of the cannula in accordance with an illustrative embodiment.
Figure 1C:
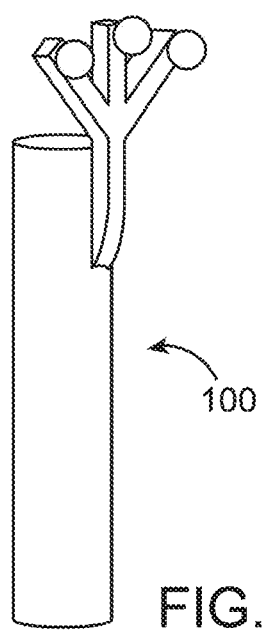
Figure 1D:
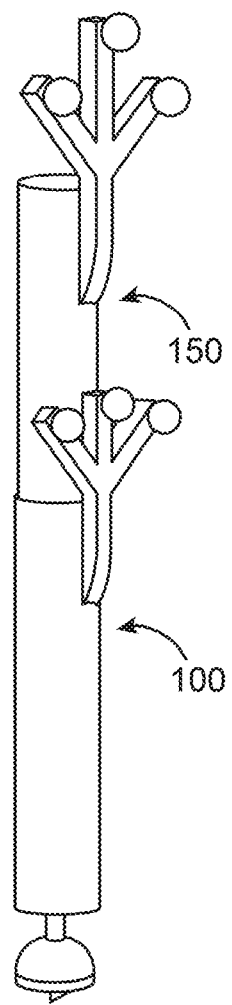
FIG. 1D depicts the rotary tool after being inserted into central hole of the cannula in accordance with an illustrative embodiment.

FIG. 1C depicts the rotary tool 150 in anticipation of being inserted into the central hole 120 (from FIG. 1A) of the cannula 100 in accordance with an illustrative embodiment. FIG. 1D depicts the rotary tool 150 after being inserted into central hole 120 (from FIG. 1A) of the cannula 100 in accordance with an illustrative embodiment.

Figure 2:
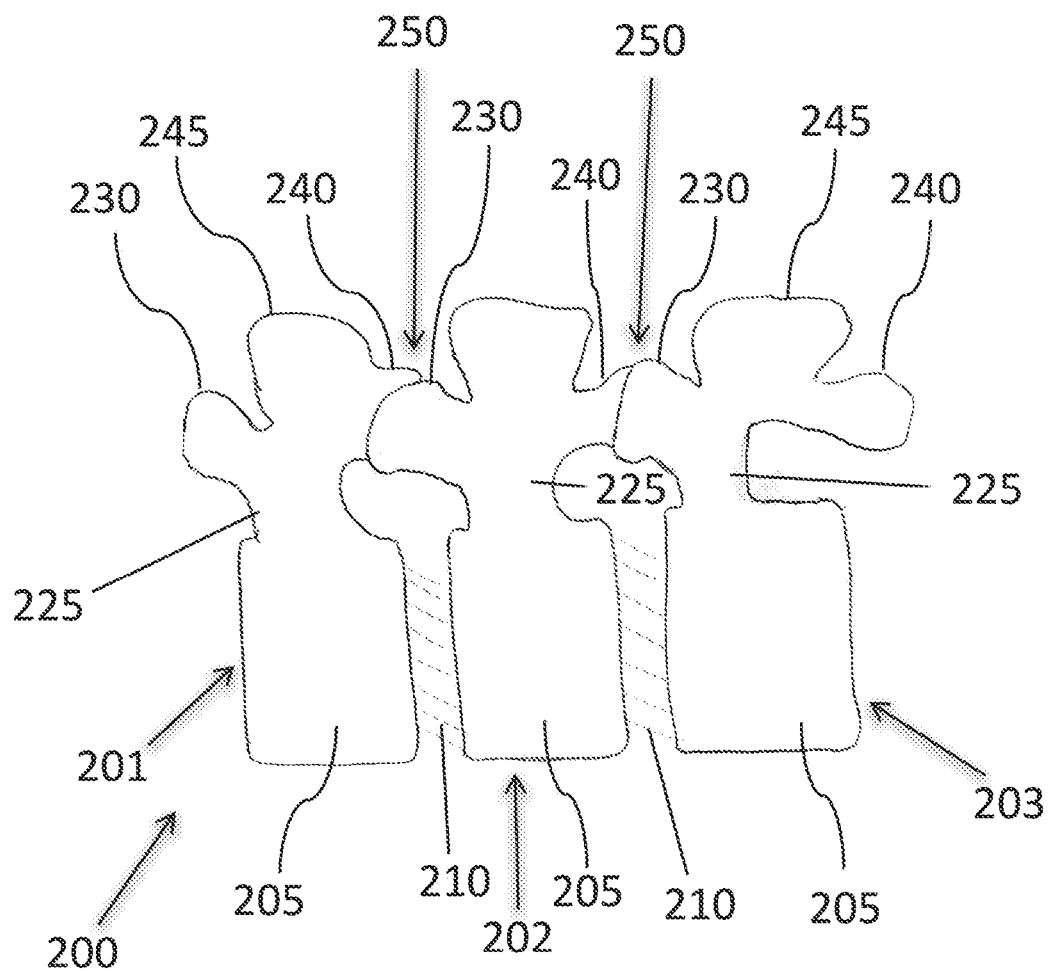
FIG. 2 depicts a lateral view of a lumbar spine segment in accordance with an illustrative embodiment.

FIG. 2 depicts a lateral view of a lumbar spine segment 200 in accordance with an illustrative embodiment. Lumbar spine segment 200 includes vertebrae 201, 202, and 203, with vertebra 201 the most cephalad and vertebra 203 the most caudal. Each of the vertebrae 201, 202, and 203 includes a vertebral body 205, bilateral pedicles 225 (although only the unilateral pedicle is seen in this lateral view), bilateral superior articular processes 230 (although only the unilateral superior articular process is seen in this lateral view), bilateral inferior articular processes 240 (although only the unilateral inferior articular process is seen in this lateral view), and a spinous process 245. An intervertebral disk 210 is located between cephalad and caudal bodies. A facet joint 250 is formed by the articulation of an inferior articular process 240 with a superior articular process 230. The facet joints are bilateral, although only one side is seen in this lateral view.

Figure 4A:
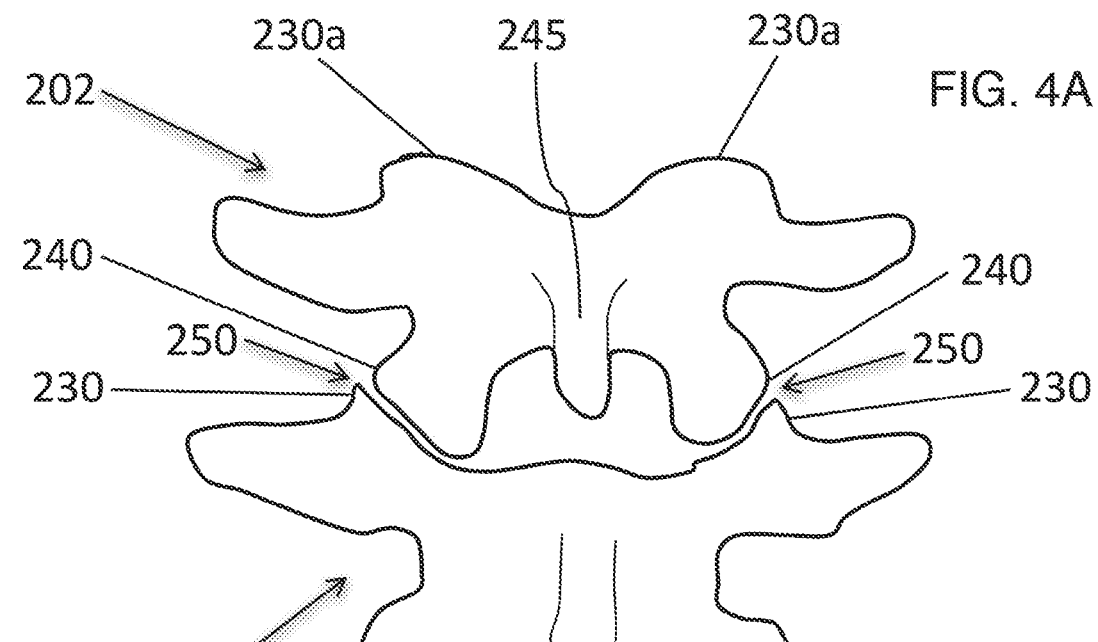
FIG. 4A is a posterior view of a depiction of a vertebral segment that includes a cephalad vertebra and a caudal vertebra in accordance with an illustrative embodiment.
Figure 4B:
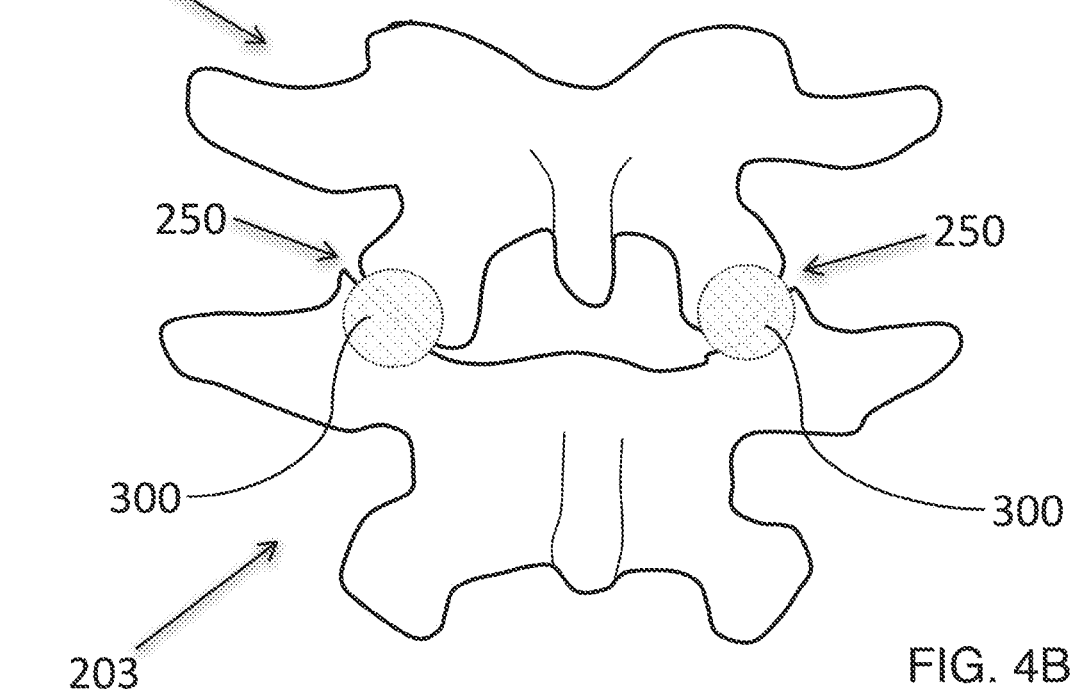
FIG. 4B is a posterior view of a depiction of a cephalad vertebra and a caudal vertebra, with facet joints (as shown in FIG. 4A) in accordance with an illustrative embodiment.

In the depiction of FIG. 2, a single vertebral level or segment may be defined as having a cephalad vertebra 201 and a caudal vertebra 202 and an intercalated disk 210, or a cephalad vertebra 202 and a caudal vertebra 203 and an intercalated disk 210. It should be noted that the terms "cephalad" and "caudal" with respect to an individual vertebra are relative terms. That is, a vertebra may be referred to as cephalad in one vertebral segment and caudal in another vertebral segment, or referred to as caudal in one vertebral segment and cephalad in another vertebral segment. In any given vertebral segment, the vertebra that is located closest to the patient's head is referred to as the cephalad vertebra, and the vertebra that is located furthest from the patient's head is referred to as the caudal vertebra. Thereby a cephalad vertebral body has bilateral inferior articular processes 240 (although only the unilateral inferior articular process 240 is seen in this lateral view) that articulate with bilateral superior articular processes 230 (although only the unilateral superior articular process 230 is seen in this lateral view) of a caudal vertebral body. The articulating relationship of articular processes 230 and 240 collectively forms bilateral facet joints 250 (although only the unilateral facet joint 250 is seen in this lateral view). This depiction therefore shows two vertebral levels or segments, one segment formed by vertebrae 201 and 202, the other segment formed by vertebrae 202 and 203, and each segment having bilateral left and right facet joints 250 (though in this lateral spine depiction, only a unilateral facet joint 250 is shown; FIG. 4A and FIG. 4B depict bilateral facet joints).

FIG. 3A depicts a lateral view of the lumbar spine segment 200, including facet joint 250, and a cannula 100 docked onto facet joint 250, in accordance with an illustrative embodiment. FIG. 3B depicts a lateral view of the lumbar spine segment 200 with facet joint 250, a cannula 100 docked onto facet joint 250, and the rotary tool 150 inserted into the cannula 100, in accordance with an illustrative embodiment. Rotary tool bit 155 can thus be used to create a void in the facet joint 250.

Figure 3C:
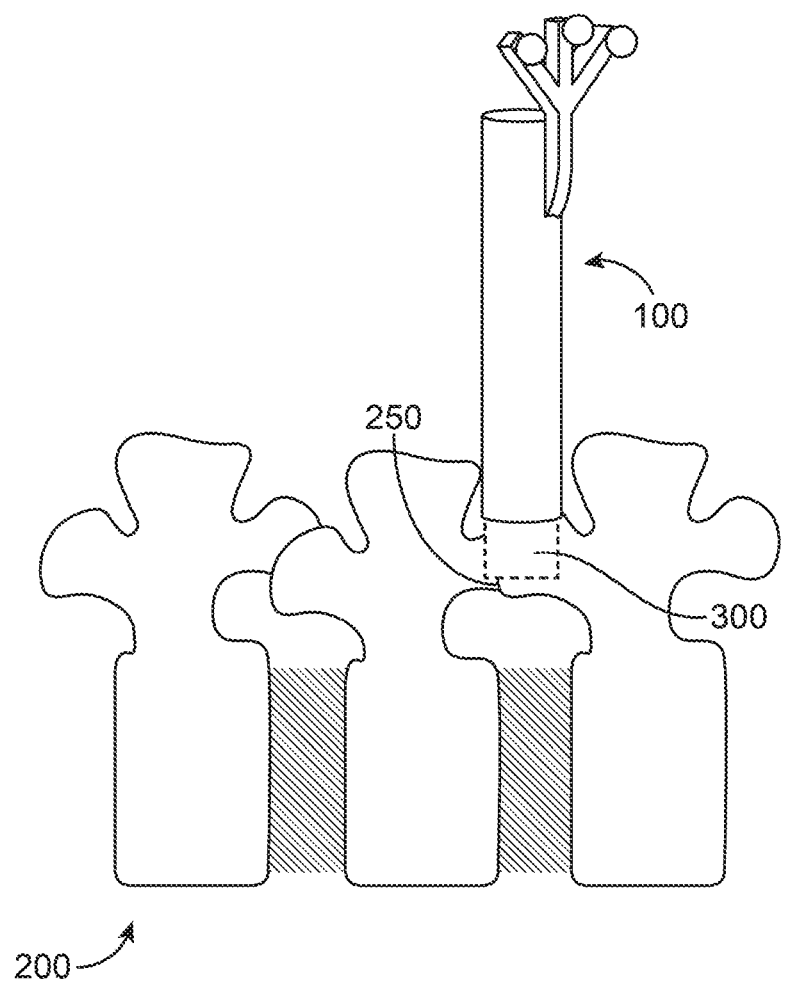
FIG. 3C depicts a lateral view of the lumbar spine segment, including the facet joint, and the cannula docked onto the facet joint, in accordance with an illustrative embodiment.

FIG. 3C depicts a lateral view of the lumbar spine segment 200, including the facet joint 250, and the cannula 100 docked onto the facet joint 250, in accordance with an illustrative embodiment. The rotary tool 150 (from FIG. 3B) has been removed, showing void 300 in facet joint 250 that was created by rotary tool bit 155 (from FIG. 3B). In some embodiments, void 300 could be filled with bone graft and/or other bone growth promoting material, in order to promote a fusion across facet joint 250.

FIG. 4A is a posterior view of a depiction of a vertebral segment that includes a cephalad vertebra 202 and a caudal vertebra 203 in accordance with an illustrative embodiment. Inferior articular processes 240 of cephalad vertebra 202 articulate with the superior articular processes 230 of caudal vertebra 203, forming facet joints 250. Spinous processes 245 are also shown, as are the superior articular processes 230*a* of cephalad vertebra 202 and the inferior articular processes 240*a* of caudal vertebra 203, for anatomical orientation.

FIG. 4B is a posterior view of a depiction of a cephalad vertebra 202 and a caudal vertebra 203, with facet joints 250, as shown in FIG. 4A, in accordance with an illustrative embodiment. Now depicted are voids 300 that have been created by the rotary tool bit (not shown) as described in FIG. 3B and FIG. 3C. Bone graft and/or a bone growth promoting material is placed into void 300, in order to produce the biologic environment that is designed to produce a bony fusion across facet joints 250.

FIG. 4C is a first cross-sectional depiction of a vertebra 202, with facet joints 250 (as shown in FIG. 4A) in accordance with an illustrative embodiment. Articular processes 240 of the cephalad vertebra 201 (not shown, see FIG. 4A)

articulate with the articular processes 230 of vertebra 202, forming facet joints 250. Spinous process 245, vertebral body 205, and pedicles 225 are shown for anatomical orientation.

FIG. 4D is a second cross-sectional depiction of the vertebra 202, with facet joints 250 (as shown in FIG. 4A) in accordance with an illustrative embodiment. Dashed lines 250α and 250β are drawn parallel to the facet joint, matching and representing the facet joint angle and orientation.

FIG. 4E is a cross-sectional depiction of the vertebra 202 with cannulas 100 docked on the facet joints in accordance with an illustrative embodiment. FIG. 4F is a cross-sectional depiction of the vertebra 202 with bone graft or bone growth promoting material 300 placed in voids in the facet joints in accordance with an illustrative embodiment.

Referring to FIG. 4E, dashed lines 250α and 250β are parallel to the facet joints (see FIG. 4D), matching, and representing, the facet joint angles. Dashed line 250c represents the midline of the vertebral body, drawn in the sagittal plane, otherwise called the midsagittal vertebral line. Dashed line 250d represents the midline of the vertebral body, drawn in the coronal plane, otherwise called the midcoronal vertebral line. Angles α and β represent different facet joint angles with respect to the midline sagittal plane, and may be referred to as the facet joint angle. For ease of reference, angle α is shown as formed between facet joint angle line 250α and sagittal plane line 250a, with 250a being parallel to dashed line 250c, where the dashed line 250c represents the midline of the vertebral body, drawn in the sagittal plane. For ease of reference, angle β is shown as formed between facet joint angle line 250β and sagittal plane line 250b, with 250b being parallel to dashed line 250c, with dashed line 250c representing the midline of the vertebral body, drawn in the sagittal plane. As an illustrative example using angle α, if facet joint angle line 250α was parallel to midsagittal line 250c, the facet joint angle would be 0 degrees; and if facet joint angle line 250α was parallel to midcoronal line 250d, the facet joint angle would be 90 degrees. Therefore, facet joint angle α may be anywhere between 0 and 90 degrees. While facet angles α and β are shown as illustrations of representative facet angles, in the human body, any facet angle between 0 and 90 degrees is possible and may occur in the human body.

Figure 5:
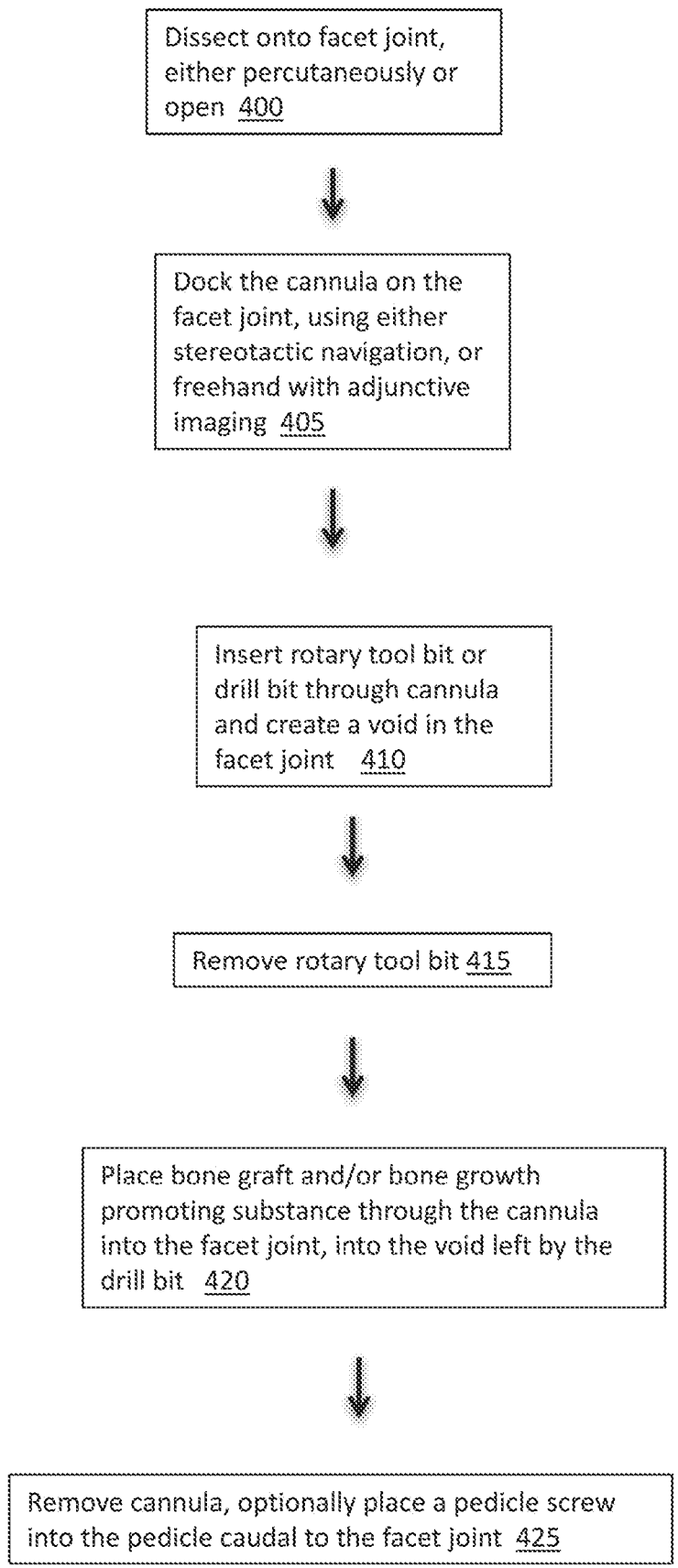
FIG. 5 is a flow diagram depicting operations to perform a percutaneous facet fusion in accordance with an illustrative embodiment.

FIG. 5 is a flow diagram depicting operations to perform a percutaneous facet fusion in accordance with an illustrative embodiment. In alternative embodiments, fewer, additional, and/or different operations may be performed. Additionally, the use of a flow diagram is not meant to be limiting with respect to the order of operations performed. In an operation 400, the surgeon dissects onto the facet joint, either percutaneously or in an open surgery. If percutaneous, the incision location may be determined with the use of fluoroscopy or stereotactic navigation. Alternatively, any other method(s) known to those of skill in the art may be used.

In an operation 405, the surgeon docks the cannula on the facet joint, using either stereotactic navigation, or freehand with adjunctive imaging. In an illustrative embodiment, an imaging system is used to determine both the docking location (e.g., on the facet joint) for the cannula and the docking angle for the cannula at the docking location. The imaging system can do this based on the position of one or biological markers that have implanted in the patient, based on the position of one or more markers mounted to the cannula, based on images/locations of anatomical features of the patient, etc.

In an operation 410, the surgeon then inserts a rotary tool bit or drill bit through the cannula and creates a void in the facet joint. In an operation 415, the surgeon then removes rotary tool bit 415. In an operation 420, the surgeon places bone graft and/or bone growth promoting substance through the cannula into the facet joint, into the void left by the rotary tool bit. In an operation 425, the surgeon removes the cannula, and optionally places a pedicle screw into the pedicle caudal to the facet joint. In other embodiments, one or more of these operations can be performed by a robotic arm as opposed to a surgeon. For example, the robotic arm can be controlled by a computing system that is in communication with the imaging system. The robotic arm can be therefore be controlled hold the cannula, to position the cannula at a docking location identified through imaging, to move the passive markers on the cannula if they interfere with the positioning of the cannula, position the cannula at an appropriate angle at the docking location, insert the rotary tool into the cannula, determine a depth at which to drill into the facet joint, create a cavity in the facet joint using the rotary tool, insert the bone graft or other material, etc.

In an illustrative embodiment, any of the operations described herein can be performed by a computing system that includes or is in communication with an imaging system. The imaging system can include a computed tomography (CT) system, an x-ray system, a magnetic resonance imaging (MRI) system, ultrasound, positron-emission tomography (PET), etc. The imaging system can be used to automatically identify biological features of the patient and/or features of surgical instrumentation within the patient such that a surgeon or automated system (e.g., robotic surgical system) is able to safely and efficiently perform a fusion procedure. For example, the imaging system can be used to identify muscles, ligaments, skin, neural elements, facet joints, etc. of a patient such that a surgeon can access the patient with minimal invasiveness.

In one embodiment, a marker can be inserted into a target area of the patient (e.g., near the spinal cord), and the imaging system can identify the marker within the patient to help perform imaging and navigation. For example, the marker can be of a certain type of material (e.g., metal) or have a certain property (e.g., radioactive) that allows the marker to be detected in response to an emission of light from a light source. Upon emission of light from the light source and detection of the marker, the marker and imagery of the patient can be presented on a display such that the surgeon is able to manipulate tools and equipment within the patient without causing injury. In an illustrative embodiment, any of the surgical equipment described herein can also include one or more markers that are designed to be detected by the imaging system. For example, as discussed herein, the cannula and/or the rotary tool can each include one or more passive markers that are used to assist the surgeon with navigation and positioning of the tools.

Figure 6:
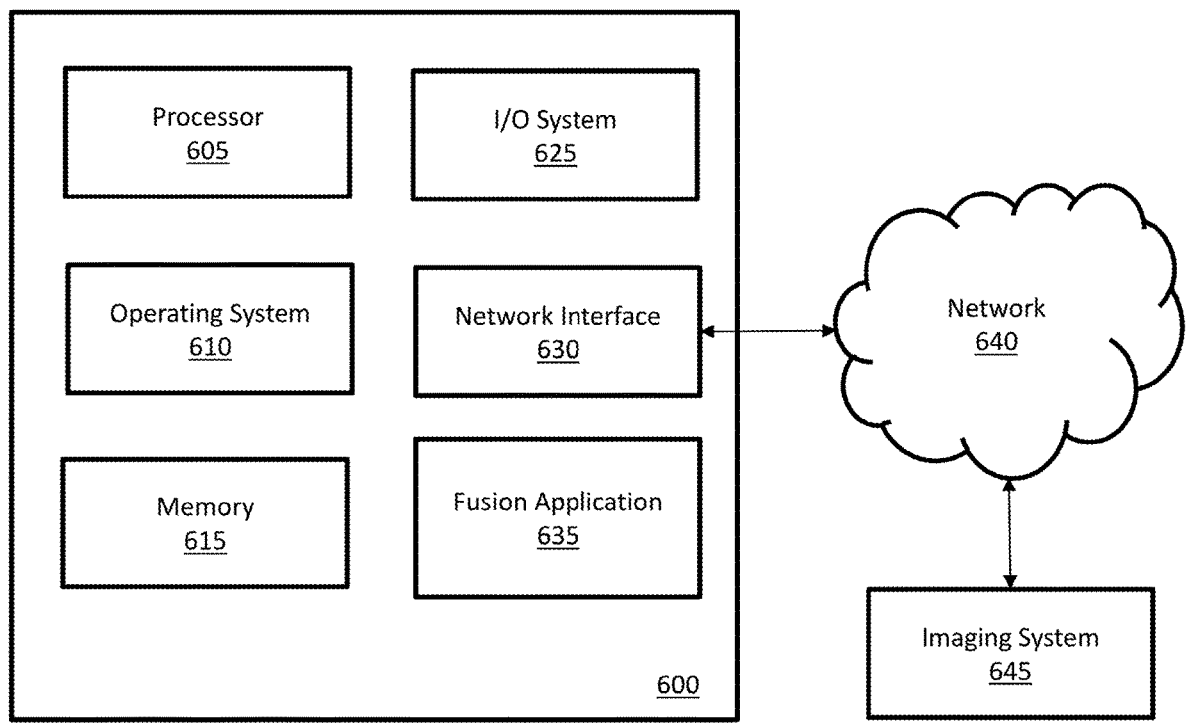
FIG. 6 is a block diagram of a computing system for a spinal fusion system in accordance with an illustrative embodiment.

FIG. 6 is a block diagram of a computing system 600 for a spinal fusion system in accordance with an illustrative embodiment. The computing system 600 includes a processor 605, an operating system 610, a memory 615, an I/O system 625, a network interface 630, and a fusion application 635. In alternative embodiments, the computing system 600 may include fewer, additional, and/or different components. The components of the computing system 600 communicate with one another via one or more buses or any other interconnect system. In an illustrative embodiment, the computing system 400 can be part of a laptop computer, desktop computer, tablet, part of an imaging system, etc.

The processor 605 can be any type of computer processor known in the art, and can include a plurality of processors and/or a plurality of processing cores. The processor 605 can include a controller, a microcontroller, an audio processor, a graphics processing unit, a hardware accelerator, a digital signal processor, etc. Additionally, the processor 605 may be implemented as a complex instruction set computer processor, a reduced instruction set computer processor, an x86 instruction set computer processor, etc. The processor 605 is used to run the operating system 610, which can be any type of operating system.

The operating system 610 is stored in the memory 615, which is also used to store programs, network and communications data, peripheral component data, light coupling data such as wavelength information, material information, material dimensions, the fusion application 635, and other operating instructions. The memory 615 can be one or more memory systems that include various types of computer memory such as flash memory, random access memory (RAM), dynamic (RAM), static (RAM), a universal serial bus (USB) drive, an optical disk drive, a tape drive, an internal storage device, a non-volatile storage device, a hard disk drive (HDD), a volatile storage device, etc.

The I/O system 625 is the framework which enables users and peripheral devices to interact with the computing system 600. The I/O system 625 can include a mouse, a keyboard, one or more displays, a speaker, a microphone, etc. that allow the user to interact with and control the computing system 600. The I/O system 625 also includes circuitry and a bus structure to interface with peripheral computing devices such as power sources, USB devices, peripheral component interconnect express (PCIe) devices, serial advanced technology attachment (SATA) devices, high definition multimedia interface (HDMI) devices, proprietary connection devices, etc. In an illustrative embodiment, the I/O system 625 is configured to receive inputs and operating instructions from the user.

The network interface 630 includes transceiver circuitry that allows the computing system to transmit and receive data to/from other devices such as remote computing systems, servers, websites, etc. The network interface 630 enables communication through the network 640, which can be in the form of one or more communication networks and devices. For example, the network 640 can include a cable network, a fiber network, a cellular network, a wi-fi network, a landline telephone network, a microwave network, a satellite network, etc. and any devices/programs accessible through such networks. The network interface 630 also includes circuitry to allow device-to-device communication such as Bluetooth® communication.

The fusion application 635 includes hardware and/or software, and is configured to perform any of the operations described herein. Software of the fusion application 635 can be stored in the memory 615. As an example, the fusion application 635 can include computer-readable instructions to control and communication with an imaging system 645. Alternatively, the computing system 600 can be incorporated into the imaging system 645. The fusion application 635 can also include computer-readable instructions to determine a location of anatomical features of a patient (e.g., skin, bone, joints, muscles, ligaments, etc.), determine a location of markers (e.g., a dye) that mark anatomical features of the patient, determine a location of passive markers mounted to a cannula or rotary tool, etc. The fusion application 635 can also cause movement of one or more passive markers mounted on the cannula/rotary tool to avoid injury to the patient, where the movement is based on data from the imaging system 645, such as the location of markers and/or anatomical features. The fusion application 635 can also determine a depth at which a cavity in the facet joint is to be made. Further, in embodiments in which a robotic surgical arm is used to perform one or more operations in a procedure, the fusion application 635 can control the robotic surgical arm.

In some embodiments, the fusion application 635 can be used to identify a facet joint between two vertebra such that a fusion can be performed at the facet joint. The fusion application 635 can use the imaging system 645 to identify the facet joint or any other location in the patient upon which an operation is to be performed. The fusion application 635 can also be used to determine an appropriate angle at which to drill into the facet joint, and in some embodiments can cause a robotic arm of the system to position the cannula and rotary tool at the appropriate angle. The fusion application 635 can further be used to remotely control the drill or other rotary tool that is used to put a recess/opening in the bone.

The computing system 600 is in communication with the imaging system 645 via the network 640. In an illustrative embodiment, the imaging system 645 can be used to perform any of the imaging operations described herein, and can include a CT system, a laser system, an ultrasound system, a PET system, etc. The imaging system 645 can be used to determine the locations of anatomical structures of the patient, the rotary tool, the cannula, biological markers within the patient, etc.

The components described herein can be made in a variety of lengths and/or shapes to accommodate various patient anatomies and surgeon preferences. The components can be made from stainless steel, plastic, titanium, titanium-alloy, cobalt-chrome, or any suitable material that is able to withstand the biomechanical stresses under which they will be placed.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A system for percutaneous or open facet joint fusion, the system comprising:
   an imaging system configured to identify a docking location on a facet joint between a first vertebra and a second vertebra of a patient;
   a computing system in communication with the imaging system, wherein the computing system is configured to determine a docking angle at which to position a cannula at the docking location, wherein the docking angle is specific to the patient and is determined based on analysis of the facet joint of the patient;
   the cannula, wherein the cannula is configured to be positioned at the docking location on the facet joint at the docking angle; and
   a rotary tool that is configured to mount within the cannula, wherein the rotary tool is configured to create a void in the facet joint by way of the cannula, and wherein the void is configured to receive a bone graft or bone growth promoting material.

2. The system of claim 1, wherein the cannula includes one or more markers, and wherein the imaging system is configured to identify the one or more markers when the cannula is positioned within the patient.

3. The system of claim 2, wherein the cannula includes an actuator configured to move the one or more markers.

4. The system of claim 3, further comprising a computing system in communication with the imaging system, wherein the computing system is configured to activate the actuator to move the one or more markers based at least in part on the docking location on the facet joint.

5. The system of claim 2, wherein the one or more markers is mounted on a navigation arm that is attached to an exterior surface of the cannula.

6. The system of claim 5, wherein the navigation arm includes a plurality of arms, and wherein each of the one or more markers is mounted to an arm in the plurality of arms.

7. The system of claim 1, wherein the rotary tool includes one or more markers mounted thereto, and wherein the imaging system is configured to identify the one or more markers on the rotary tool.

8. The system of claim 1, wherein the imaging system is configured to display a position of the cannula relative to one or more anatomical features of the patient such that the cannula can be docked without damage to the one or more anatomical features.

9. The system of claim 1, further comprising the bone graft or bone growth promoting material.

10. The system of claim 9, wherein the bone graft or bone growth promoting material is configured for placement through the cannula and into the void.

11. The system of claim 9, further comprising a tamp that is configured to fit within the cannula such that the bone graft or bone growth promoting material can be forced into the void.

12. The system of claim 1, wherein the cannula includes one or more first markers and the rotary tool includes one or more second markers that differ from the one or more first markers, and wherein the imaging system is configured to distinguish between the one or more first markers and the one or more second markers.

13. The system of claim 1, wherein the imaging system is configured to identify one or more biological markers within the patient and one or more markers mounted to the cannula, and wherein the imaging system is configured to display the positional relationship between the one or more biological markers and the one or more markers.

14. A method for performing percutaneous or open facet joint fusion, the method comprising:
- identifying, by an imaging system, a docking location on a facet joint between a first vertebra and a second vertebra of a patient;
- determining, by a computing system in communication with the imaging system, a docking angle at which to dock a cannula at the docking location, wherein the docking angle is specific to the patient and is determined based on analysis of the facet joint of the patient;
- docking the cannula at the docking location on the facet joint at the docking angle; and
- creating, by a rotary tool that is configured to mount within the cannula, a void in the facet joint, wherein the void is configured to receive a bone graft or bone growth promoting material.

15. The method of claim 14, wherein the cannula includes one or more markers, and further comprising identifying, by the imaging system, the one or more markers when the cannula is positioned within the patient.

16. The method of claim 15, wherein the cannula includes an actuator, and further comprising moving, by the actuator, the one or more markers from a first position to a second position.

17. The method of claim 14, wherein placing the bone graft or bone growth promoting material into the void comprises forcing the bone graft or bone growth promoting material through the cannula and into the void.

18. The method of claim 14, further comprising displaying, by the imaging system, a position of the cannula relative to one or more anatomical features of the patient such that the cannula can be docked without damage to the one or more anatomical features.

* * * * *